United States Patent
Gruhler

(10) Patent No.: US 10,548,578 B2
(45) Date of Patent: Feb. 4, 2020

(54) AUTOMATIC REGISTRATION OF THE PENETRATION DEPTH AND THE ROTATIONAL ORIENTATION OF AN INVASIVE INSTRUMENT

(71) Applicant: Karl Storz SE & Co. KG, Tuttlingen (DE)

(72) Inventor: Ulrich Gruhler, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 296 days.

(21) Appl. No.: 14/662,641

(22) Filed: Mar. 19, 2015

(65) Prior Publication Data
US 2015/0265367 A1 Sep. 24, 2015

(30) Foreign Application Priority Data
Mar. 19, 2014 (DE) .................. 10 2014 103 728

(51) Int. Cl.
*A61B 17/00* (2006.01)
*A61B 1/00* (2006.01)

(52) U.S. Cl.
CPC .... *A61B 17/00234* (2013.01); *A61B 1/00055* (2013.01); *A61B 2562/043* (2013.01)

(58) Field of Classification Search
None
See application file for complete search history.

(56) References Cited

U.S. PATENT DOCUMENTS 4,715,714 A 12/1987 Gaechter et al.
5,437,290 A 8/1995 Bolger et al.
2003/0069474 A1 4/2003 Couvillon, Jr.
2005/0075558 A1 4/2005 Vecerina et al.
2005/0228452 A1* 10/2005 Mourlas ............ A61B 1/00071
607/3
2005/0272971 A1 12/2005 Ohnishi et al.
(Continued)

FOREIGN PATENT DOCUMENTS

DE 3424806 C2 4/1988
DE 19750698 A1 5/1998
(Continued)

OTHER PUBLICATIONS

European Search Report Application No. EP 15 15 9337 Completed: Jul. 27, 2015; dated Aug. 4, 2015 8 pages.

Primary Examiner — Thomas J Hong
Assistant Examiner — Shahdeep Mohammed
(74) Attorney, Agent, or Firm — Whitmyer IP Group LLC

(57) ABSTRACT

A device for automatically registering the penetration depth of an invasive instrument into an opening and the rotational orientation of an invasive instrument in an opening of a body with the aid of a length-selective and rotation-selective pattern applied to the surface of the instrument, wherein the device has a sensor embodied to surround the instrument in a ring-shaped manner. According to the invention, the sensor is embodied for registering the length-selective and rotation-selective pattern and embodied and provided for the temporary arrangement in the region of the opening for the insertion of the invasive instrument. The device according to the invention has an evaluation unit for evaluating the penetration depth and the rotational orientation of an invasive instrument on the basis of the registered selective pattern.

21 Claims, 6 Drawing Sheets

(56) References Cited

U.S. PATENT DOCUMENTS

| | | | |
|---|---|---|---|
| 2007/0249901 | A1 | 10/2007 | Ohline et al. |
| 2008/0262473 | A1 | 10/2008 | Kornblau et al. |
| 2012/0316486 | A1* | 12/2012 | Cheung .................. A61C 1/082 602/48 |
| 2013/0204095 | A1* | 8/2013 | Mark ............... A61B 17/32001 600/249 |
| 2014/0336462 | A1* | 11/2014 | Tojo .................. A61B 1/00073 600/117 |

FOREIGN PATENT DOCUMENTS

| | | | |
|---|---|---|---|
| DE | 19812609 A1 | | 10/1999 |
| DE | 102009060522 A1 | | 6/2011 |
| WO | WO 2013/066194 | * | 5/2013 |
| WO | 2013115231 A1 | | 8/2013 |
| WO | WO2013/115231 | * | 8/2013 |

* cited by examiner

| Penetration depth | Rotation in degrees | | | | |
|---|---|---|---|---|---|
| | 0° | 72° | 144° | 216° | 288° |
| 1 | 00100 | 00010 | 00001 | 10000 | 01000 |
| 2 | 00110 | 00011 | 10001 | 11000 | 01100 |
| 3 | 00101 | 10010 | 01001 | 10100 | 01100 |
| 4 | 10110 | 01011 | 10101 | 11010 | 01101 |
| 5 | 00111 | 10011 | 11001 | 11100 | 01110 |
| 6 | 10111 | 11011 | 11101 | 11110 | 01111 |

Fig.4

AUTOMATIC REGISTRATION OF THE PENETRATION DEPTH AND THE ROTATIONAL ORIENTATION OF AN INVASIVE INSTRUMENT

FIELD OF THE INVENTION

The invention relates to a device for automatically registering the penetration depth of an invasive instrument into an opening and the rotational orientation of an invasive instrument in an opening of a body, and a system for automatically registering the penetration depth and rotational orientation of an invasive instrument.

BACKGROUND OF THE INVENTION

DE 34 24 806 C2 has disclosed an automated digital leveling instrument, which enables an electronic rod readout. To this end, a code pattern of black and white elements is applied onto the leveling rod, a part of which code pattern is imaged on a spatially resolving detector with the aid of the telescopic optics of the electronic leveling instrument. Here, the information from the code pattern situated in the field of view of the telescope is used to obtain the desired height measurement value by comparison with the code pattern of the leveling rod stored as a reference code pattern in the leveling instrument.

Furthermore, the patent document D3 198 12 609 C2 has disclosed a method for determining the position and rotational orientation of a surgical microscope or a surgical tool such as e.g. a scalpel or endoscope. To this end, the object to be examined is registered by a plurality of cameras distributed in space and the spatial coordinates, including the rotational orientation, of the object to be examined are established from the image information. With the aid of information about the body of the patient in respect of the position and location thereof, it is possible to register, evaluate and display the precise spatial location of the object to be examined, in particular of the surgical microscope or the surgical instruments, in respect of the operation site of the human. With the aid of this information, it is also possible to guide the surgical instruments in a fully automated manner. This method was found to be very complex and complicated since it must process a large amount of data relating to the body to be operated on and relating to the image information registered by a plurality of camera-like measurement heads in order to determine reliable information in respect of the penetration depth and the rotational orientation of a medical invasive instrument or object.

Moreover, flexible endoscopes and flexible borescopes that exhibit line markings with length specifications that specify the distance of the line markings to the distal end of the shank on the flexible shank thereof are known. With the aid of these markings, the user of the flexible endoscope can estimate the penetration depth into the body during an operation, e.g. of a human, or, in the case of a borescope, estimate the penetration depth into e.g. the sewage pipe by virtue of reading the last identifiable line marking with the distance specification in the region of the body opening or the pipe opening. This type of estimating the penetration depth is very inaccurate and not automated.

SUMMARY OF THE INVENTION

The invention is based on the object of specifying a device for automatically registering the penetration depth and the rotational orientation of an invasive instrument, which enables reliable information in respect of penetration depth and in respect of rotational orientation and, in the process, exhibits a relatively simple setup. A further object of the invention consists of specifying a system for automatically registering the penetration depth and the rotational orientation of an invasive instrument with the aforementioned advantages.

These objects according to the invention are achieved by a device for registering the penetration depth and the rotational orientation of an invasive instrument according to the invention as claimed.

The device according to the invention for automatically registering the penetration depth of an invasive instrument into an opening and the rotational orientation of an invasive instrument in an opening of a body renders it possible to register the penetration depth or the rotational arrangement with the aid of a length-selective and rotation-selective pattern arranged on the surface of the instrument and to output this to a user when necessary. Here, the invasive instrument can firstly be a technical instrument, e.g. a rigid or flexible borescope, by means of which, for example, examinations of a sewage canal or an examination of e.g. a gas turbine can take place, but it can also be medical invasive instruments, e.g. flexible or rigid endoscopes, by means of which minimally invasive operations can be performed in the human or animal body, or else endoscopic instruments, by means of which manipulations can be undertaken within the scope of minimally invasive operations. By way of example, these manipulations can contain simple displacement of tissue, severing and removal of tissue or RF coagulation. In all of these invasive instruments, it may be very important for the user to obtain reliable information about the penetration depth of the instrument in the respective opening, be this during a minimally invasive operation in a body opening of a human or animal or be this a technical opening, e.g. a pipe opening.

The device according to the invention contains a sensor which has a ring-shaped embodiment and which is suitable for surrounding the invasive instrument, the penetration depth and rotational orientation of which are to be measured. The sensor with the ring-shaped embodiment registers the length-selective and rotation-selective pattern on the invasive instrument, in particular on an optical basis, and forwards this information to an evaluation unit for evaluating the penetration depth and rotational orientation of the invasive instrument.

As a result of the arrangement, according to the invention, in the region of the opening, in particular directly at the opening of the body, through which the invasive instrument is introduced, it is possible to register the pattern situated there selectively on the introduced invasive instrument and register and evaluate the reliable penetration depth or the rotational orientation of the instrument and make this available for possible output to the user. Here, according to the invention, the temporary arrangement of the sensor is implemented in such a way that the sensor with the ring-shaped embodiment is made to overlap the opening of the body in such a way that the invasive instrument, the penetration depth or rotational orientation of which is to be registered, can be introduced through the overlapping opening and meaningful information in respect of the penetration depth or in respect of the rotational orientation of the instrument can be measured.

As a result of the direct measurement, i.e. registration and evaluation, of the length-selective and rotation-selective pattern in the region of the opening of the body, a very meaningful and simple device according to the invention is developed, which directly and automatically, and also reliably, registers the required information such as penetration depth and the rotational orientation in relation to the invasive instrument introduced into the opening of the body.

According to the invention, the pattern on the surface of the invasive instrument is embodied in a length-selective manner, i.e. the pattern changes continuously or quasi-continuously with the distance from the distal end of the invasive instrument. Here, the pattern at a specific distance is selective for this distance and therefore so unique that, by way of the pattern registration, a statement about the distance from the distal end of the position of the pattern element can be obtained with the aid of the sensor and the associated evaluation unit. By way of example, using this, it is possible to obtain information that a flexible technical borescope has been introduced 7.48 meters into a cable channel.

With the aid of a rotationally selective pattern on the surface of the instrument, which is applied over the whole length or at least over part of the length of the invasive instrument and for example shows a characteristic marking at a position of the circumference, it is possible to register this characteristic marking on the circumference selectively with the aid of the ring-shaped sensor in such a way that information about the rotational orientation of the invasive instrument can be obtained therefrom with the aid of the evaluation unit. Since this characteristic marking in the ring-shaped sensor is registered by the latter and the latter is situated in the direct vicinity of the opening, this allows a statement to be about the rotational orientation of the invasive instrument in the opening of the body and subsequently this allows an output or a different type of use of this information to be carried out.

In this case, it has particularly proven its worth to use a length-selective and rotational-selective pattern and evaluate these two items of information together in time such that the device according to the invention allows both information about the penetration depth of the invasive instrument into the opening and also, simultaneously, information about the rotational orientation of the invasive instrument in the opening of a body to be obtained and, according to the invention, to be supplied for use. This use can firstly be implemented by means of forwarding the corresponding information to the user, in particular the surgeon, for example with the aid of a display unit by means of an optical indicator, i.e. in the form of a display, but also, alternatively or additionally, be implemented as, for example, information for guiding the invasive instrument, which may optionally occur in fully or partly automated manner.

Another embodiment of the invention exhibits a system for automatically registering the penetration depth and the rotational orientation of an invasive instrument with a device according to the invention and an invasive instrument, which has a length-selective and rotation-selective pattern on the surface thereof. This pattern, which is applied to the whole or part of the length of the invasive instrument, has regions of different colors and/or different brightness levels on the circumference of the instrument. Here, the different regions of the pattern arranged on the circumference of the instrument can have two or more different colors and/or different brightness levels, which are unambiguously distinguishable from one another. By way of the increased number of different utilized colors or brightness levels, which may also be combined, it is possible to significantly increase the information content of the pattern in the case of a given number of utilized regions. By way of example, if use is made of five regions and only two different colors which can be registered with the aid of the sensor, it is possible to display at most $2^5$, i.e. 32, different selective items of information in respect of the length and/or the orientation with the aid of the pattern. However, if 10 different colors and/or brightness levels are used, there already are $10^5$, i.e. 100 000, different items of information in respect of length and/or orientation in the case of five utilized regions. Here, the pattern is applied along the invasive instrument in such a way that the arrangement of the regions of different color or brightness, applied to the circumference, is selectively dependent on the distance from the distal end of the invasive instrument and therefore represents a unique item of distance information. In respect of the information relating to the rotational orientation, reference is made to the above-described concept of the characteristic marking of a circumferential position. If the length-selective pattern additionally exhibits a characteristic position on the circumference, it is possible not only to register and evaluate the length-selective information but, additionally, also to register and evaluate the rotational orientation. Here, there is no need to add the length information from one shank end in order to establish the current position.

As a result of the interaction according to the invention between the invasive instrument with the characteristic length-selective and rotation-selective pattern arranged over the length thereof or part of the length thereof and the device for registering the penetration depth and the rotational orientation of the invasive instrument, it is possible to obtain very reliable and certain as well as simple information in relation to the penetration depth or the rotational orientation and supply this to a further use. By way of example, penetration depth and rotational position can be stored together with a timestamp or an image recorded at this position. Thus, it is subsequently possible to assign an image to a specific position of the instrument in the body.

A preferred system for automatically registering the penetration depth and the rotational orientation of an invasive instrument uses a binary pattern of a plurality of regions with two different colors and/or brightness levels, e.g. black and white, on the surface of the invasive instrument, wherein the various arrangements applied to the circumference of the instrument are selected from the plurality of regions in such a way that these have a Hamming distance of at least 1. As a result, it is possible to distinguish the arrangements at different length positions in such a clear manner that, even in the case of a readout error, the obtained information in respect of the penetration depth or the distance to the distal end of the invasive instrument can nevertheless be uniquely and reliably registered and evaluated and supplied to a further use. According to the invention, this leads to some of the possible arrangements being dispensed with and, as a result thereof, the resolution of the length information and/or the orientation information being significantly restricted. By way of example, in this arrangement according to the invention of the regions of the pattern in the form of a binary code, for example with five bits, i.e. five regions, it is not possible to use $2^5$, i.e. 32, resolution steps, but it is only possible to use six different arrangements with said Hamming distance. Here, according to the invention, the resolution is sacrificed for the increased reliability and meaningfulness of the information relating to the penetration depth and the rotational orientation. This was found to be by all means sufficient, precisely when using rigid invasive instruments, such as e.g. in the case of rigid endoscopes. The use of binary codes was found to be very reliable since the sensors can very reliably distinguish between the different regions. The reduced resolution caused thereby, in particular in respect of the desired Hamming distance of the utilized pattern arrangements, is compensated for by the number of utilized regions of the patterns being increased. Particularly in the case of short, rigid invasive instruments, use is made of at least five regions for a binary pattern with a 5-bit length; in the case of longer invasive instruments, use is made of 10 or more regions in order to increase the resolution.

Moreover, it has particularly proven its worth to develop the system for automatically registering the penetration depth and the rotational orientation of an invasive instrument in such a way that the utilized pattern on the circumference of the invasive instrument has at least one transition from one color and/or brightness to another and at least one inverse transition. It was found to be particularly preferable to only use such arrangements of the regions in the pattern which are also unique in the case of cyclical transposition of the regions. As a result, it is also possible to detect the rotational orientation in addition to the information in respect of the penetration depth since each arrangement on the circumference of the instrument per se has a unique sequence of the regions, which also differs from all other arrangements in the case of cyclical transposition of the regions. This ensures that, in the case of a continuous pattern applied over the complete circumference of the invasive instrument, a unique and selective arrangement is provided in each case independently of the start of the evaluation along the circumference, and unique information can be obtained and extracted in respect of the rotational orientation of the instrument.

An advantageous development of the device according to the invention is distinguished by virtue of having a ring-shaped housing, in which the ring-shaped sensor is arranged, and by virtue of an evaluation unit being integrated in the housing in addition to the ring-shaped sensor. The ring-shaped sensor, which surrounds the invasive instrument with the length-selective and rotation-selective pattern on the surface thereof and which registers said pattern, forwards the sensor signal thereof to the evaluation unit in the common ring-shaped housing such that the evaluation of the sensor signals as penetration depth information or rotational orientation information is performed within the compact ring-shaped housing, which typically forms a device according to the invention. As a result of this embodiment of the device according to the invention, a very compact unit is developed, which enables application in the region of the opening, particularly in the case of operations on a human or animal, without having to worry about a relevant impediment of the surgeons. Moreover, this device according to the invention was found to be well sterilizable as a result of this ring-shaped embodiment of the housing and therefore suitable for medical use. Furthermore, the ring-shaped housing ensures a reliable and secure protection of the ring-shaped sensor with evaluation unit integrated into the housing.

It was found to be particularly advantageous to embody the device according to the invention in such a way that the ring-shaped housing is embodied in a hinged manner. Here, the ring-shaped housing with the integrated ring-shaped sensor can be composed of a plurality of ring parts, which can be separated from one another, wherein these can remain partially connected to one another by flexible, in particular hinge-shaped connection elements and therefore can be pivoted in relation to one another about this connection point. As a result of this multi-part embodiment of the housing for hinging, it is possible to put together and arrange the device in a simple and reliable manner at the point of use, i.e. in the region of the opening around the invasive instrument, which was possibly already introduced into the opening of the body, in such a way that the ring-shaped housing with the ring-shaped sensor surrounds the invasive instrument to be registered in a ring-shaped manner and, as a result thereof, it is possible to register and evaluate the surface by means of the ring-shaped surrounding sensor over the whole circumference of the invasive instrument. As a result, very reliable and simple handling is ensured, even under difficult conditions. In particular, this device according to the invention also enables a subsequent application of the device according to the invention in the case where the requirement of penetration depth information or orientation information has only become necessary at a later stage of the operation. In this case, it is possible to dispense with a removal of the invasive instrument from the opening, which substantially simplifies the handling and makes damage to the instrument or the body less probable. Moreover, it is possible to significantly reduce the handling time of the invasive instrument.

As a result of the optional provision of an optically transparent inner housing on the inner side of the device or of the ring-shaped housing of the device, it is possible, firstly, to reliably ensure an optical registration of the pattern on the surface of an invasive instrument introduced into the ring-shaped housing or into the ring-shaped device and, secondly, to ensure by means of the transparent inner housing a mechanical, reliable separation of the sensitive ring-shaped sensor from the invasive instrument or the surroundings, in particular the opening. As a result, it is possible, firstly, to preclude damage to the sensor, but, in the case of a medical application of the device, it is also possible to prevent an impairment of the operation surroundings e.g. by an influence of the substances, in particular the metallic substances or chemical substances of the integrated ring-shaped sensor or of the evaluation unit, which are separated by the housing and the transparent inner housing. As a result, it is possible to largely preclude a contamination of the body to be operated on. Incidentally, the device was found to be particularly well-suited to cleaning and, in particular, sterilizing as a result of the suitable selection of the material of the transparent inner housing, which substantially increases the field of application of the invention and the quality of the registered penetration depth information or rotational orientation information.

In addition to the option of arranging a single integral elongate sensor in a ring-shaped manner in the device, it was found to be advantageous to use a plurality of individual sensor elements which together form the sensor and to arrange these in a ring-shaped manner in the device in such a way that they can completely register the inner region of the ring, so that an invasive instrument introduced into this inner region can be sensed by means of the ring-shaped sensor formed from a plurality of sensor elements. What this ensures is that a selective pattern applied to the surface of the invasive instrument can be reliably and confidently registered and fed to an evaluation. As a result of this, very compact optimized individual sensor elements can be connected to form a ring-shaped overall sensor, for example by virtue of the sensor elements being connected to one another electrically by way of common circuitry. By way of example, the circuitry can be formed by a ring-shaped circuit board which, in particular, is embodied as a ring-shaped flexible circuit board. The signals from the individual sensor elements are fed by way of the circuit board to the evaluation unit arranged, in particular, on the circuit board and combined there to form the sensor signal and evaluated to provide information about the penetration depth and the rotational orientation.

Here, it was found to be particularly advantageous to embody the individual sensor elements as individual CCD sensor elements, CMOS sensor elements and/or reflection-light photoelectric sensor elements. These sensor elements were found to be very suitable for this application since, firstly, they can be embodied in a very compact manner and, in particular, they are suitable for reliably registering a selective pattern according to the invention on the surface of an invasive instrument in the near-field region, i.e. in the inner region of the ring-shaped sensor. In addition to the option of only using a single type of sensor element, it has also proven its worth to use combinations of different types of exemplary sensor elements together. Here, the sensor elements are preferably arranged and embodied or selected in such a way that they alternately have an overlap in the registration regions thereof such that a reliable registration of the pattern is ensured, even if a single sensor element fails. The additional optionally multiple items of information from the different sensor elements are evaluated in this case with the aid of the evaluation unit in such a way that these multiple items of information do not lead to erroneous information.

Furthermore, it has proven its worth to realize the ring-shaped sensor by virtue of a plurality of optical waveguides being used in such a way that the one ends thereof are arranged in the housing in a ring-shaped manner in such a way that the ends thereof point in the direction of the inner space of the ring-shaped arrangement of the ends of the optical waveguides and are able to receive light from the inner space. The other ends of the optical waveguides are respectively assigned to one or more sensor elements in such a way that the sensor elements are able to register and sense the light from the inner space transmitted by the optical waveguides. Here, the sensor elements are arranged in an array-shaped manner, wherein this is preferably implemented as a linear array. As a result, it is possible to achieve a very compact arrangement of sensor elements which, firstly, are well integrable into a common housing, in particular into the ring-shaped housing.

The array of sensor elements is preferably arranged on a circuit board to which the evaluation unit is also attached. As a result, it is possible to reduce the number of components and ensure a reliable and secure integration into the device with the housing. CCD sensor elements, CMOS sensor elements and/or reflection-light photoelectric sensor elements have proven their worth as particularly preferred sensor elements. In addition to the exclusive use of a single type of sensor element, it has also proven its worth to use a combination of different variants of one type of sensor element, for example different CCD sensor elements, or else a combination of different types of technology for sensor elements such as CCD sensor elements with reflection-light photoelectric sensor elements. As a result of this, the areas of application of the invention can be increased by the fitting selection of the utilized sensor elements.

In a further embodiment, the ring-shaped housing with the ring-shaped sensor has an in particular ring-shaped light source, which illuminates the inner region enclosed by the ring-shaped housing in a ring-shaped manner. In particular, the illumination is implemented through the transparent inner housing.

As a result of providing a light source, preferably with a ring-shaped embodiment, for illuminating the inner space of the ring-shaped sensor of the device according to the invention, it is possible to ensure the area of application of the device according to the invention even under difficult external circumstances, i.e. in the case of low or non-existent external light. As a result, it is possible to be independent of external light sources and, as a result thereof, it is possible to ensure the precondition for reliable registration and identification of the selective patterns on an introduced invasive instrument. The inherent light source which, in particular, is implemented as a ring-shaped light source according to the invention ensures a sufficient illumination of the surface with the selective pattern of the introduced invasive instrument independently of external further conditions. Precisely the embodiment of a ring-shaped light source, which corresponds to the ring-shaped sensor in terms of the arrangement thereof in the housing, ensures, firstly, a reliable whole-area illumination of the inner space of the ring-shaped arrangement and, at the same time, a corresponding whole-area registration of the inner space of the ring-shaped arrangement of the sensor. Here, the invasive instrument to be registered is introduced into these inner spaces corresponding to one another. Here, it was found to be particularly advantageous to provide a transparent inner housing which reliably separates the in particular ring-shaped light source with the ring-shaped sensor from the inner space in a mechanical, chemical and biological manner and, as a result thereof, prevents reciprocal unwanted influencing.

In addition to the option of providing a single ring-shaped light source, it has proven its worth, precisely when providing a hinged ring-shaped housing, to provide a plurality of individual light sources which are arranged in a ring-shaped manner, together form the ring-shaped light source and, as a result thereof, illuminate the inner space of the ring-shaped sensor as completely as possible.

The power supply and actuation of the individual light sources are preferably implemented via the same structure, e.g. in the form of a ring-shaped circuit board, as in the case of the ring-shaped sensor or the sensor elements arranged in a ring-shaped manner. As a result of this, it is possible to obtain high integration and a reduction of components, which reduces the volume of the device and enables a compact ring-shaped housing for this device.

Additionally, it has also proven its worth to ensure the illumination of the inner space with the aid of optical waveguides, into which light is coupled at one end by means of one or more central light sources and wherein said light is guided via the optical waveguides to in each case the other end and decoupled there. Here, these other ends are arranged around the inner space of the ring-shaped sensor in a ring-shaped manner, as a result of which an illumination of this inner space which is as complete as possible is implemented. Preferably, optical waveguides are not only used for illumination purposes, but other optical waveguides are used for sensing parallel thereto. Here, these optical waveguides differing in terms of their function can be arranged alternating with one another in a ring-shaped manner around the inner space and a very high density of optical waveguide fiber ends can thus be achieved. This leads to a very high resolution of the ring-shaped sensor with a uniform and strong illumination. According to the invention, there can be a plurality of sensor optical waveguides for each illumination optical waveguide in a common ring-shaped arrangement; i.e., in addition to the option of forming multiple mutually separated ring-shaped arrangements, a single common ring-shaped arrangement of alternating optical waveguide ends is preferably selected.

In order to increase the reliability of the information in respect of the penetration depth and in respect of the rotational orientation, it has particularly proven its worth to provide not only a single ring-shaped sensor for registering the length-selective and rotation-selective pattern, but to provide a plurality, in particular two or three, of such ring-shaped sensors, which are arranged parallel to one another and at a distance from one another. Each of these ring-shaped sensors is suitable for registering the inner region of the ring-shaped sensor structure thereof and forwarding this to an evaluation. As a result of this, it is possible for different regions, which are at a distance from one another, of an invasive instrument with an applied selective pattern introduced into the inner region to be registered parallel to one another. Depending on the different registration regions, the various sensors respectively register different selective patterns of the overall pattern, typically leading to differing sensor information. By way of example, different penetration depths or distances from the distal end of the invasive instrument emerge as the registration regions are offset from one another and differ accordingly. During the evaluation of the various sensor signals by the evaluation unit, the latter considers the distances of the ring-shaped sensors from one another such that a correction of the sensed values is implemented and uniform, correct information in respect of the penetration depth and in respect of the rotational orientation can be obtained. This was found to be particularly reliable and certain.

The electrical and possibly optical connection of the individual components of the device according to the invention is preferably implemented with the aid of a circuit board arranged in the housing, said circuit board being embodied in particular in a ring-shaped or at least partial ring-shaped manner and at least partly enclosing the ring-shaped sensor or the ring-shaped light source. As a result of this type of ring-shaped or partial ring-shaped circuit board, it is possible to ensure a very reliable and secure connection between the electric or electronic or optoelectronic components of the device, which, in conjunction with the preferably ring-shaped housing, also ensures additional mechanical stability and integrity. By using this ring-shaped or partial ring-shaped circuit board, which can also be embodied as a flexible circuit board, in particular as a partly flexible circuit board, it is possible to design the device with the housing thereof, which preferably has a ring-shaped embodiment, in a very compact manner and, as a result thereof, make it particularly well employable, precisely in the medical field.

In addition to the option of providing the device with the housing with a dedicated and not separate output unit and outputting the evaluated information in respect of the penetration depth and in respect of the rotational orientation on the housing of the device itself, it has particularly proven its worth to provide a separate output unit, which is preferably connected wirelessly. This output is suitable for providing the evaluated information in respect of the penetration depth into a body and in respect of the rotational orientation of the invasive instrument in the body to a user, who is e.g. the surgeon during an operation on a human. This is preferably implemented with the aid of an optical representation, for example with the aid of a display. On the display, the penetration depth is preferably specified using an alphanumeric representation but, alternatively, a graphic, symbolic representation can also be used. By contrast, the rotational orientation is preferably used in the form of a graphic, symbolic representation, whereas the alternative alphanumeric representation, for example in degrees, is possible but less conventional. The registration of the exact penetration depth, in particular in centimeters or parts of centimeters, is of great importance here, which is why the alphanumeric representation has particularly proven its worth. Compared to the alphanumeric representation, the symbolic representation of the rotational orientation can be registered more easily and quickly and therefore more reliably by the user. Additionally or alternatively, it has also proven its worth also to provide the information to be output acoustically to the user.

The wireless transmission of the information from the device to the evaluation unit was found to be the preferred type of transmission, with a wired transmission also being found to be suitable since use of wireless transmission technologies in the operating theater always contains a certain electromagnetic noise potential for other vital components of the operating theater.

When use is made of the device according to the invention, the device is arranged in the region of the opening of the body, into which the invasive instrument is introduced. Here, precisely during use in the medical field, it has proven its worth to provide the ring-shaped housing of the device according to the invention for in particular detachable fastening to the body in the region of the opening and, particularly in this case, directly at the opening of the body. Here, detachable fastening is preferably implemented by an adhesive connection, for example in the style of an adhesive bandage, or by a tape-shaped fixation, for example by means of a loop or by means of negative pressure areas, by means of which the housing is securely suctioned onto the body, in particular onto the e.g. human skin, and thereby ensures reliable, in particular detachable, fastening in the region of the opening. As a result of the detachable implementation of the fastening, it is possible to remove the device from the body without residue. To this end, the device or the housing of the device is embodied in such a way that the adhesive connection, for example the adhesive strips or adhesive bandages, the ring-shaped tape fixation or else the negative pressure areas, can be connected reliably and securely to the device or the housing of the device.

Additionally, particularly in the case of technical applications of the device according to the invention, it has proven its worth to provide fixation elements or receptacles for such fixation elements, such as e.g. screws or nails, which can be introduced and fixed in the technical body which is intended to be examined with the aid of the invasive instrument.

When using the device according to the invention in the medical or veterinary sector, it was found to be very advantageous to integrate the device at least partly, in particular completely, into a nip protection, which is arranged in the region of the opening through which the invasive instrument is introduced, or to connect it to the latter. As a result of this connection between the nip protection, which prevents jamming and, as a result thereof, damage to the tissue in the region of the opening when inserting and removing the invasive instrument, a very compact, easy to handle and reliable structure is provided, said structure ensuring reliable information in respect of the penetration depth and in respect of the rotational orientation of an invasive instrument.

In the following text, the invention will be described on the basis of various examples in the figures. The invention is not restricted to these examples.

BRIEF DESCRIPTION OF THE DRAWINGS

In detail:

FIG. 4 shows a table of an exemplary binary encoded pattern, which is length-selective and rotation-selective.

DETAILED DESCRIPTION OF THE INVENTION

Figure 1:
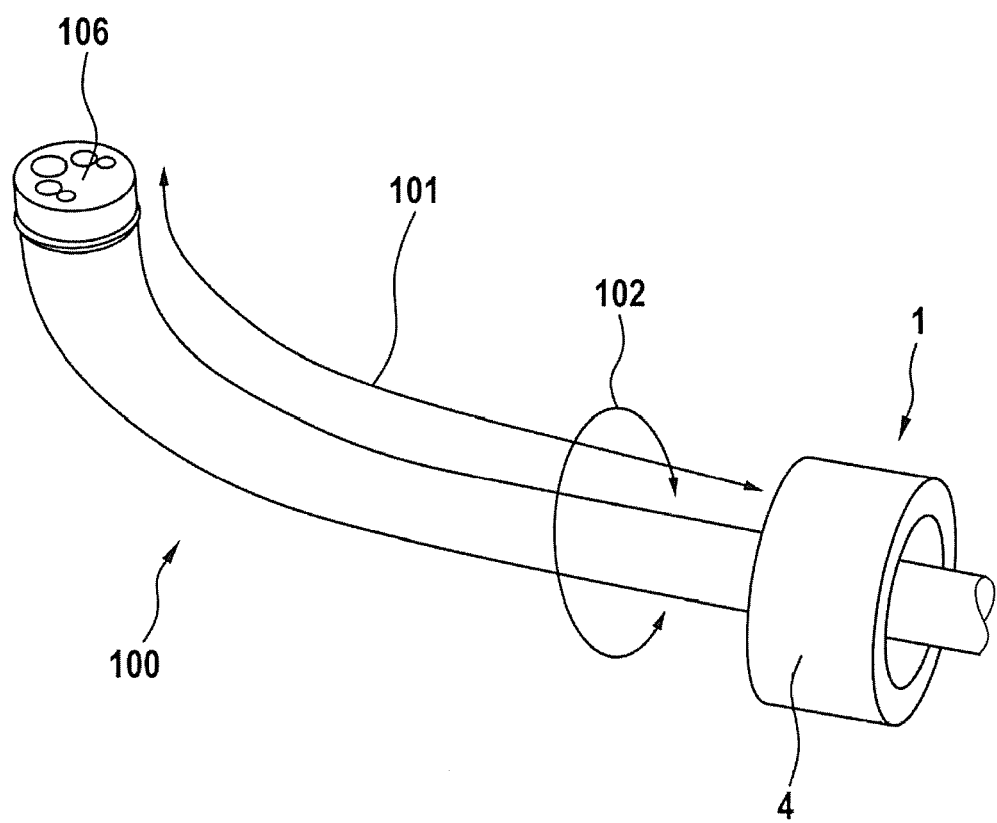
FIG. 1 shows an exemplary, schematic system according to the invention with a device according to the invention and an invasive instrument.

The system for automatically registering the penetration depth 101 and the rotational orientation 102 of an invasive instrument 100, depicted in FIG. 1, shows a device 1, which encloses the invasive instrument 100 in a ring-shaped manner. The device 1 for automatically registering the penetration depth 101 and the rotational orientation 102 has a ring-shaped housing 4, in which an evaluation unit 3 (not depicted in FIG. 1) and a ring-shaped sensor 2 are arranged in an integrated manner.

The ring-shaped sensor 2 registers the surface 103 of the invasive instrument 100 and the patterns 104 arranged thereon optically. According to the invention, a length-selective and rotation-selective pattern 104 is arranged on the surface 103 of the instrument 100, said pattern being registered and evaluated by the device 1. Since the device 1 with the housing 4 is applied in the direct vicinity of the opening of e.g. a minimally invasive operation opening in a human body, through which opening the invasive instrument 100, which is embodied here as a flexible endoscope, is introduced, the distance of the device 1 according to the invention from the distal end 106 of the invasive instrument 100 can be registered with the aid of the length-selective and rotation-selective pattern 104 in the internal region of the device 1. To this end, this information is contained in code in the length-selective and rotation-selective pattern in the registration region of the device according to the invention. As a result, obtaining information in respect of the penetration depth 101 of the medical invasive instrument 100 and information in respect of the rotational orientation 102 of the instrument 100 relative to the device 1 is made possible in a direct, simple and reliable manner. This information is very helpful for the reliable performance of an operation since the image generated by the flexible endoscope enables better orientation in the body of the patient.

Figure 2:
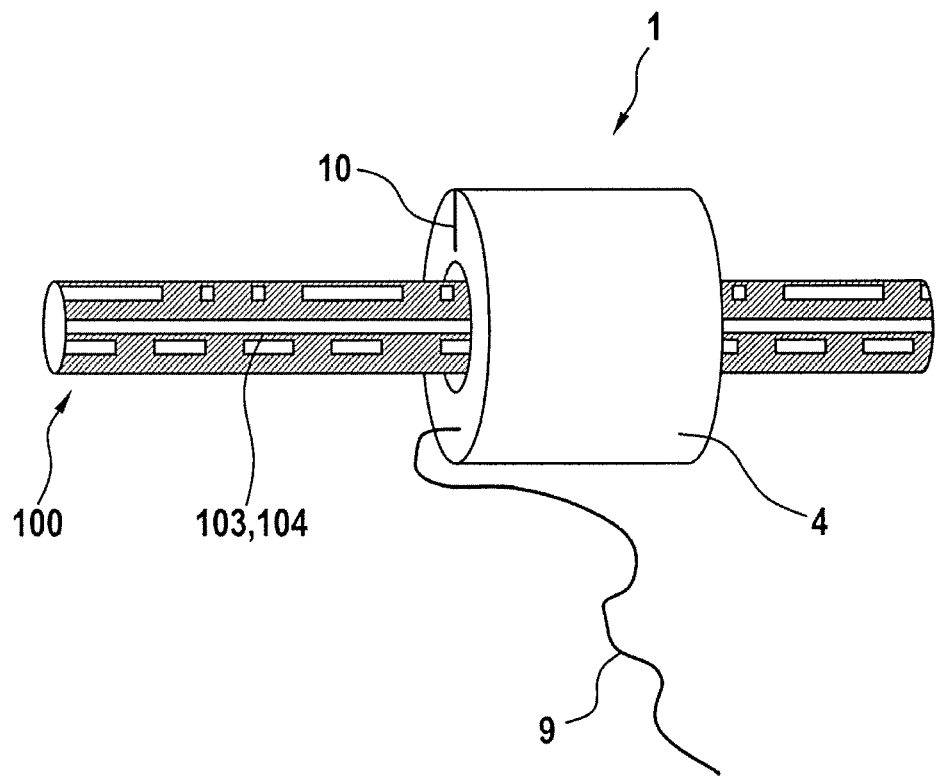
FIG. 2 shows a schematic section of an arrangement of the device according to the invention and an invasive instrument.

FIG. 2 depicts a detailed section of another exemplary device 1 according to the invention. The device 1 exhibits a hollow cylinder-shaped housing 4, through the inner cavity of which an invasive, rigid borescope 100 is guided and integrated. A selective pattern 104 is applied to the surface 103 of the borescope 100, said pattern extending over the whole surface 103 of the invasive instrument 100. Here, the whole pattern is encoded in such a manner that a sequence of black and white regions is arranged along the circumference of the surface, i.e. in the region of a cross section through the borescope 100, which black and white regions form a binary encoding of a plurality of individual bits represented by individual regions.

Figure 3:
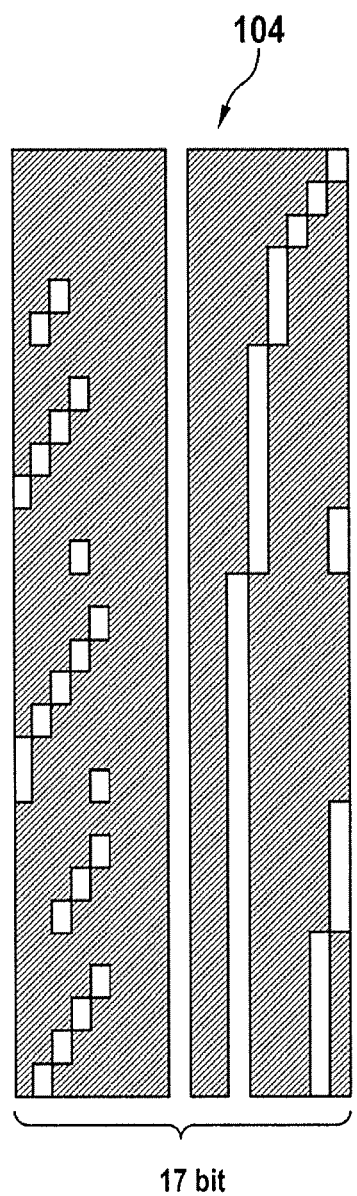
FIG. 3 shows an exemplary section of a length-selective and rotation-selective pattern.

FIG. 3 reproduces a planar representation of the pattern 104. It exhibits a width of 17 bit and is represented as a binary code of black and white regions arranged next one another. As a result of this, $2^{17}$ different items of information can, in principle, be represented by the different possible arrangements. However, according to the invention, use is not made of all possible codes, but only of those which have at least a Hamming distance from one another of 1. According to the invention, each individual code pattern contains at least one transition from white to black and, conversely, from black to white from one to the adjacent region. Additionally, use is only made of those code patterns which are embodied selectively against cyclical transposition. This means that the arrangement of the regions is unique, independently of the position of the start of the readout along the circumference around the invasive instrument 100, and that there cannot be confusion simply as a result of the different starting point of the readout. This leads to only a small part of the $2^{17}$ theoretically possible different codes actually being used in order to obtain unique rotation-selective orientation information. FIG. 3 depicts such examples for such a unique encoding in a graphic manner. As a result, it is possible, firstly, to establish the length, i.e. the distance to the distal end 106 of the borescope 100 with the aid of the device according to the invention, and, secondly, to establish the relative rotational orientation 102 at the same time.

As a result of using such a binary pattern with a length of 17 bit and a Hamming distance of 1, it is possible to encode 7710 detectable arrangements which, in the case of a borescope 100 having a length of 7.7 m, enables a length resolution and therefore a resolution of the penetration depth 101 of 1 mm. In respect of the angular tolerance, a resolution of 360°/17, i.e. 21.1°, emerges in the case of a code with a length of 17 bit. Therefore, using this pattern, it is possible to register 17 orientation levels with a distance of 21.1° in a differentiated manner and provide these to the user.

A ring-shaped sensor 2 is contained in the interior of the device 1 according to the invention or of the ring-shaped housing 4, said sensor being suited and embodied to register the circumference of the borescope 100 arranged in the inner cavity of the housing 4 and to register the pattern 104 arranged on the surface 103 of said borescope and to evaluate the penetration depth information and the information in respect of the rotational orientation 102 with the aid of the evaluation unit 3 arranged in the housing 4.

Here, the device 1 according to the invention is directly applied to the body opening of the pipe, into which the borescope 100 is introduced, and detachably connected thereto. As a result, this ensures that the registered length information of the penetration depth 101 or the registered rotational orientation 102 corresponds to the actual orientation of the borescope 100 in the opening.

Additionally, a marking 10 is arranged on the housing 4, said marking giving the user the option of conveying a reference point for the orientation information, i.e. the rotation relative to this orientation marking 10.

The information in respect of the penetration depth 101 and in respect of the rotational orientation 102 established by the device 1 is forwarded with the aid of an electric cable 9 to a separate output unit (not displayed here), which constitutes a display, and provided to the user by means of this output unit. Here, the penetration depth 101 is typically output as alphanumeric information, e.g. 1.37 m, whereas the rotational orientation information is regularly depicted as a graphic representation in the form of a larger or smaller angular segment. In accordance with his wishes, the user can also select other display forms in respect of the penetration depth 101 or in respect of the rotational orientation 102.

The table depicted in FIG. 4 shows a coding for a selective pattern which has a length of 5 bit. Here, each bit is implemented as a binary code 0 or 1. This 5 bit binary code can be applied along the circumference around the shank of the invasive instrument by means of black/white marking regions and it can be fed to the device according to the invention for automated registration. Although, in theory, $2^5$, i.e. 32, different codes, i.e. arrangements of the regions, are possible, many of the 32 possible codes are not used in view of the uniqueness of the arrangement, even in the case of a rotation, i.e. in view of cyclical transposition, and, in particular, in view of a provided Hamming distance of 1 or more; in fact, only six of these codes are used. These codes are depicted in the table in the FIG. 4. A penetration depth 101 is assigned to each of the six codes. Therefore, six different penetration depths of the invasive instrument can be distinguished with the aid of this selective code system, which is depicted in FIG. 4 in an exemplary manner and which can be applied as a black/white pattern onto the surface 103 of the invasive instrument 100.

Moreover, there can also be information or a statement in respect of the rotational orientation 102. If the invasive instrument 100 is twisted in a rotational manner, there is a change along the circumference on the surface of the invasive instrument 100 in the relative start point for the readout of the pattern by the ring-shaped sensor 2. The start point for reading out the code changes as a function of the rotational orientation 102, i.e. the measure of the twist. As a result of the aforementioned specific selection of the code, it is possible to determine the unique penetration depth 101 despite a cyclical transposition of the sequence of the code and, additionally, determine a measure for the rotational displacement and therefore the corresponding orientation on the basis of the measure of the cyclical displacement. In this case, there are five different cyclical displacement levels since a 5 bit binary code is used here. Using this, it is possible to distinguish between rotation levels of 0°, of 72°, of 144°, of 216°, and of 288°.

If the device 1 according to the invention with the sensor 2 arranged in a ring-shaped manner and the evaluation unit reads out the bit sequence 01001, it is possible to derive conclusions about the penetration depth 101 and the measure of the rotational orientation 102 from table depicted in FIG. 4. In the present case, the code 01001 would mean a penetration depth 101 of level 3 and a rotation about 144°.

As a result of the selection according to the invention of the specific arrangement of the regions, it is possible to obtain length-specific and also rotation-specific information very reliably and confidently and provide this to the user. As a result of the specific selection of this coding, it is also possible, at least to certain extent, to identify possible transmission errors and eliminate these within the scope of the evaluation process.

Figure 5:
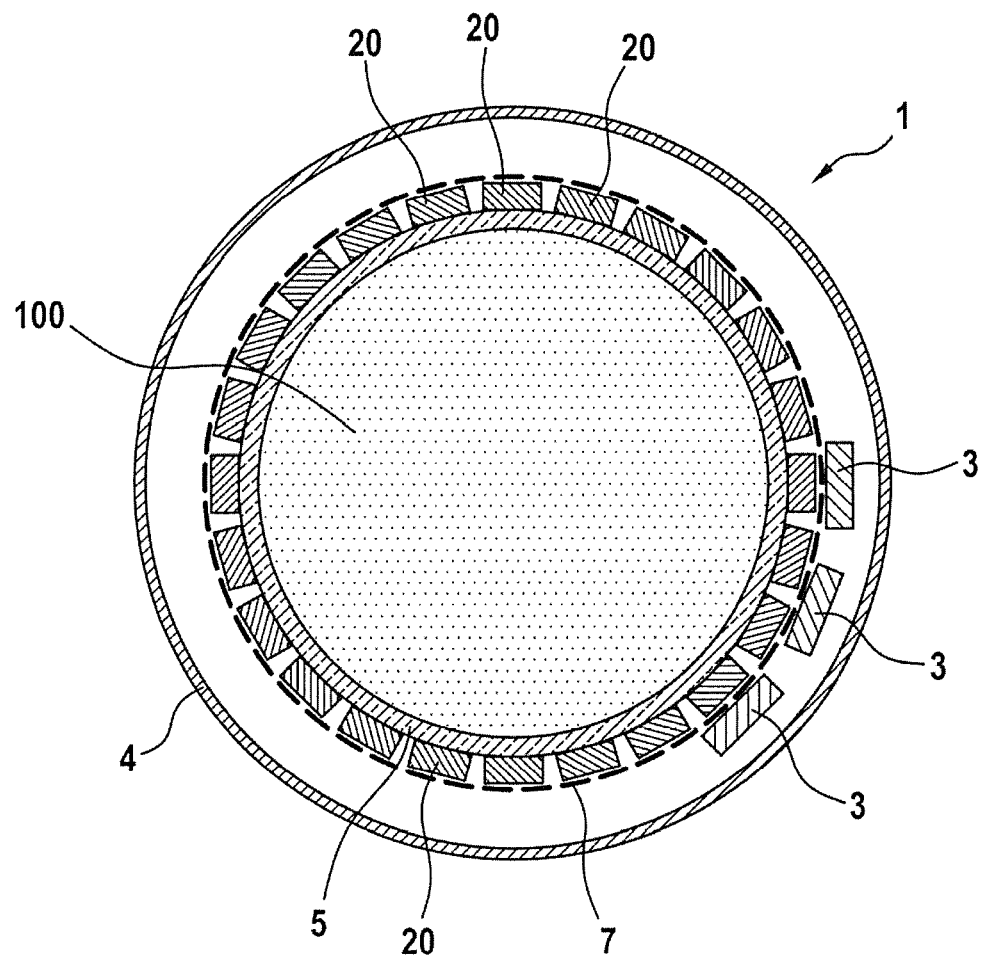
FIG. 5 shows a schematic cross-sectional illustration of an exemplary device according to the invention.
Figure 6:
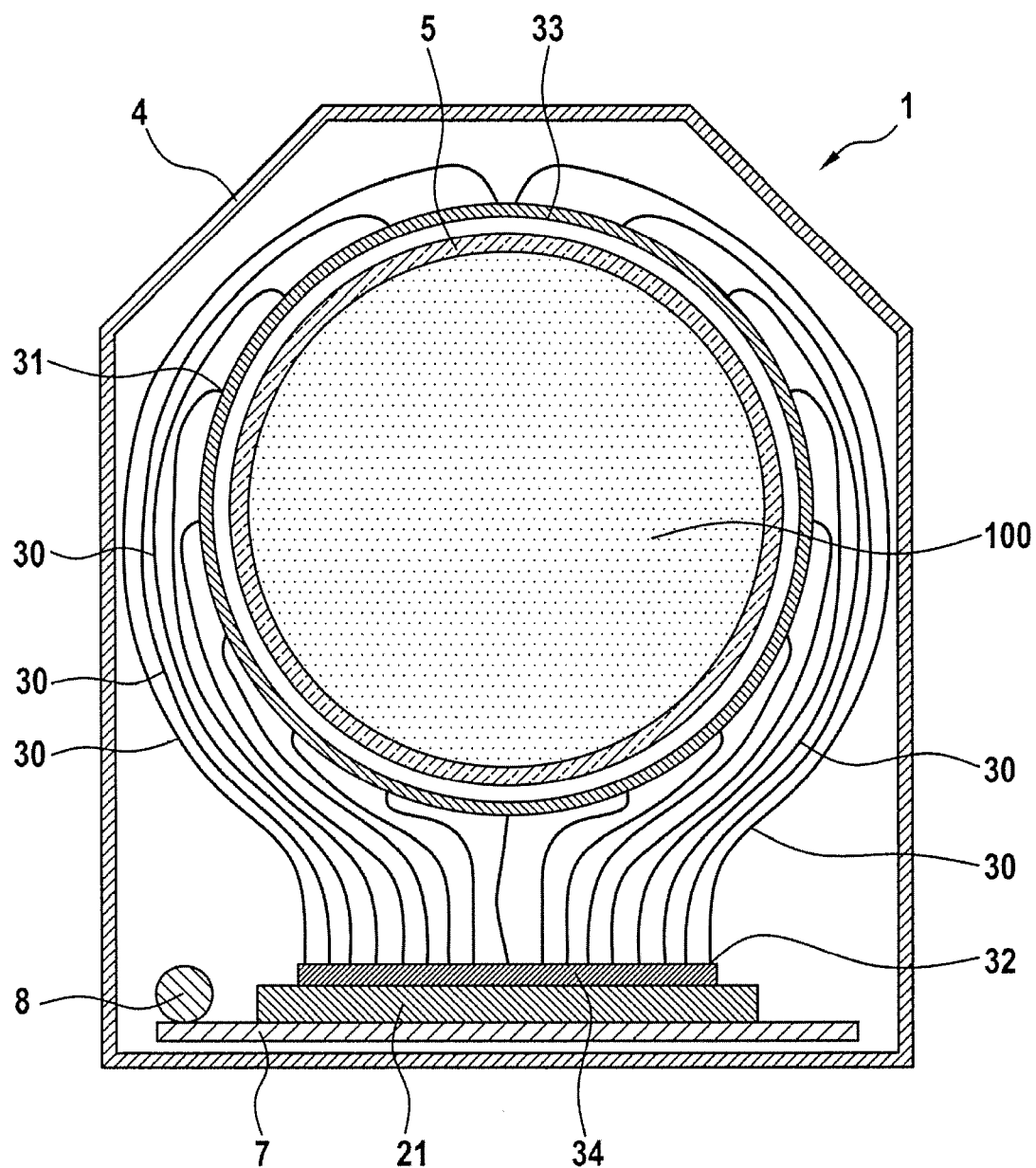
FIG. 6 shows a schematic cross-sectional illustration of a further example of a device according to the invention.

FIG. 5 and FIG. 6 depict, in the form of a cross section, two variants of the setup of the device 1 according to the invention with a hollow cylinder-shaped housing 4, which encloses, in a ring-shaped manner, the inner space into which the invasive instrument 100 to be examined is introduced, said instrument having the patterns applied to the surface thereof when used.

The housing 4 encloses the invasive instrument 100 in a ring-shaped manner, wherein an optically transparent inner housing 5 is arranged as part of the housing on the inner side of the housing 4, on the side facing the invasive instrument 100. The housing 4 and the inner housing 5 enclose the device 1 according to the invention in a sealing manner such that the device 1 according to the invention can be efficiently sterilized and can be used for use in an operating theater during a minimally invasive operation.

A multiplicity of individual sensor elements 20, which are embodied as reflection-light photoelectric sensors, are arranged in the region of the transparent inner housing 5 in the interior of the housing 4. The arrangement of the reflection-light photoelectric sensors 20 encloses the transparent inner housing 5, which is closed-off in a ring-shaped manner, in a ring-shaped manner such that the reflection-light photoelectric sensors 20 are able to reliably register the patterns 104 on the surface 103 of the invasive instrument 100, which patterns are visible through the transparent inner housing 5. Here, the number of employed reflection-light photoelectric sensors 20 is selected to be twice the number of bits which are used to encode the information with the aid of the pattern. Using this, the pattern can be uniquely determined according to the Nyquist-Shannon theorem. By way of example, if a pattern with the length of 10 bit is used, twice the number of reflection-light photoelectric sensors, i.e. 20 pieces thereof, is arranged in a circle around the transparent inner housing 5. The sensor signals formed by the reflection-light photoelectric sensors 20 are output to a circuit board 7 embodied in a ring-shaped manner, which forwards the signals to three evaluation units 3 arranged in the housing. Here, the circuit board 7 embodied in a ring-shaped manner encloses the reflection-light photoelectric sensors 20, which are arranged to form a ring, and ensures the mechanical stability of this arrangement, since said sensors are coupled to the ring-shaped circuit board 7 not only electrically, but also mechanically. As a result of this mechanically rigid coupling, a permanent, secure and reliable alignment of the reflection-light photoelectric sensors is ensured in the direction of the inner space of the hollow cylinder-shaped housing 4 through the transparent part of the inner housing 5.

As a result of the uniformly distributed arrangement of the reflection-light photoelectric sensors 20, a complete and uniform registration of the inner space is ensured such that the registration result of the device according to the invention is of high quality.

While the reflection-light photoelectric sensors 20 are arranged on the inner side of the ring-shaped circuit board 7, the evaluation units 3 are arranged on the outer side of the ring-shaped circuit board, as a result of which there is a compact arrangement of the circuit board and connected electronic components in the case of efficient registration of the desired registration region. As a result, this arrangement can be integrated into a compact ring-shaped housing 4, which has the form of a hollow cylinder, without the housing being bulky and difficult to handle. As a result, good handling is ensured, even in the difficult operation surroundings.

An alternative embodiment of the device 1 according to the invention is depicted in FIG. 6 in the form of an illustration of a schematic cross-section. A sensor which, in contrast to the device 1 in FIG. 5, has a linear array 21 of CMOS sensors is arranged in the housing 4, which encloses an inner space with the invasive instrument 100 in a ring-shaped manner. This linear array 21 is arranged on a plane circuit board 7, which has a coupling site 8 for coupling an output unit. The registered and evaluated information is transmitted to the output unit by this coupling site 8, said output unit being able to provide this information in respect of the penetration depth 101 and in respect of the rotational orientation 102 of the invasive instrument 100 to a user.

In accordance with the device 1 from FIG. 5, this housing 4 also exhibits a transparent inner housing 5, through which the surface 103 of the introduced invasive instrument 100 is registered by means of the sensor integrated into the housing 4. Here, the sensor consists firstly of the linear array 21 and a multiplicity of optical waveguides 30, the first ends 31 of which are arranged in a ring-shaped manner in a holder 33 around the optically transparent inner housing 5, and a second holder 34 for the other, second ends 32 of the optical waveguides 30. The optical waveguides 30 transmit the light from the surface 103 of the invasive instrument 100, received through the first end 31, which light, after passing through the optically transparent inner housing 5 enters into the optical waveguide 30 via the first end 31 to the other, second end 32. There, the light emerges and it is coupled to the linear array 21 of CMOS sensor elements. The sequence of the first ends 31 along the circumference of the ring-shaped holder 33 and therefore along the circumference of the optically transparent inner housing 5 or along the circumference of the invasive instrument 100 corresponds to the sequence along the linear array 21 of CMOS sensors. What this ensures in a simple and reliable manner is that the pattern 104 of bright and dark regions, which is applied to the circumference of the surface of the invasive instrument 100, is reliably transmitted to the CMOS sensor elements of the array 21 and converted there into a correct linear binary binary code word. This is evaluated by the evaluation unit (not depicted here), which is likewise arranged on the circuit board 7 and forwarded by the coupling 8 to a connected output unit as information in respect of the penetration depth 101 and/or in respect of the rotational orientation 102. Since the optical waveguides 30 have a very small diameter, it is possible to arrange a multiplicity of such optical waveguides 30 in a tightly adjacent manner along the circumference of the transparent inner housing 5 and thereby enable a very high resolution of the sensor 2. Furthermore, the arrangement of CMOS sensor elements on a linear array 21 is also possible with a high resolution in a technically simple manner, i.e. a large number of CMOS sensor elements per centimeter is possible. Overall, this leads to a very high resolution sensor 2 consisting of the array 21, made of CMOS sensor elements, the multiplicity of optical waveguides 30, the first ends 31 of which enclose the transparent inner housing 5 in a holder 33 in a ring-shaped manner, and the second ends 32, which couple to the array 21 by way of a linear or planar holder 34. This embodiment of the device according to the invention is distinguished by a very high resolution, which also renders it possible to register patterns with a large number of individual bits, i.e. on individual plane regions with different color and/or brightness, and feed these to an evaluation by the evaluation unit.

These devices 1 according to the invention enable a very secure, reliable registration of the penetration depth 101 or of the rotational orientation 102 of the introduced invasive instrument.

The invention claimed is:

1. A device for automatically evaluating penetration depth and rotational orientation of an invasive instrument during insertion of the invasive instrument into an opening of a body, the invasive instrument having an outer surface with a length-selective and rotation-selective pattern applied thereto, the device comprising:
   a sensor formed from a plurality of sensor elements embodied to enclose a whole circumference of the outer surface of the invasive instrument in a ring-shaped manner, wherein the sensor is embodied for reading the length-selective and rotation-selective pattern, wherein the sensor is embodied for temporary arrangement in a region of the opening for the insertion of the invasive instrument; and
   a signal evaluator configured to simultaneously determine a penetration depth and a rotational orientation of the invasive instrument on the basis of the length-selective and rotation-selective pattern read by the sensor;
   wherein the sensor is arranged in a ring-shaped housing; and
   wherein the ring-shaped sensor has a plurality of optical waveguides, first ends of which are arranged in the ring-shaped housing in a ring-shaped manner and second ends of which are assigned to the plurality of sensor elements, which includes at least one of (i) CCD sensor elements, (ii) CMOS sensor elements, and (iii) reflection-light photoelectric sensor elements, and which are arranged in linear array-shaped manner.

2. The device of claim 1, wherein the ring-shaped housing is embodied in such a hinged manner that the ring-shaped sensor can be opened and closed with the ring-shaped housing.

3. The device of claim 1, wherein the ring-shaped housing has an optically transparent inner housing on a side facing the invasive instrument in an operational state.

4. The device of claim 1, wherein the device has a plurality of ring-shaped sensors arranged parallel to one another for reading the length-selective and rotation-selective pattern, the sensor signal of which sensors is at least partly evaluated together with the aid of the signal evaluator.

5. The device of claim 1, wherein the ring-shaped housing has a ring-shaped or partial ring-shaped circuit board, which contains the signal evaluator, for actuation of at least one of (i) the sensor or sensors, and (ii) a light source or parts thereof.

6. The device of claim 1, wherein the device is connected to a display suitable for optically providing penetration depths and rotational orientations of an invasive instrument as evaluated by the signal evaluator to a user of the device.

7. The device of claim 1, wherein the ring-shaped housing is embodied for detachable fastening to the body.

8. The device of claim 1, wherein the signal evaluator is arranged in the ring-shaped housing.

9. The device of claim 1, wherein the signal evaluator is configured to simultaneously determine the penetration depth and the rotational orientation of the invasive instrument without first establishing a reference point for an orientation of the invasive instrument.

10. The device of claim 1, wherein the plurality of sensor elements of the sensor are configured in a uniformly distributed arrangement so as to enable a complete and uniform reading of the length-selective and rotation-selective pattern over the whole circumference defined of the outer surface of the invasive instrument.

11. The device of claim 1, wherein the plurality of sensor elements enclose the whole circumference of the outer surface of the invasive instrument in a continuous ring-shaped manner.

12. The device of claim 1, wherein a first sensor element and a second sensor element of the plurality of sensor elements have respective registration regions that overlap one another.

13. The device of claim 1, wherein the first ends of the plurality of optical waveguides inwardly face one another.

14. The device of claim 1, wherein the ring-shaped housing having has an optically transparent inner housing on a side facing the invasive instrument in an operational state; and wherein the first ends of the plurality of optical waveguides are arranged in a ring-shaped manner in a holder around the optically transparent inner housing.

15. The device of claim 1, wherein the ring-shaped housing with the ring-shaped sensor has a ring-shaped light source, which illuminates an inner region enclosed by the ring-shaped housing in a ring-shaped manner.

16. The device of claim 15, wherein the ring-shaped light source includes a plurality of light sources inwardly facing one another.

17. A system, comprising:
an invasive instrument having a length-selective and rotation-selective pattern arranged on a circumference of the invasive instrument on an outer surface thereof, which pattern consists of regions with different color and brightness, the arrangement of which selectively differs in the case of different lengths and different rotational orientations;
wherein the length-selective and rotation-selective pattern constitutes a binary pattern of regions of at least one of (i) two different colors and (ii) two different brightness levels; and
wherein the different arrangements of the regions of the length-selective and rotation-selective pattern along the instrument have a Hamming distance of at least 1;
the system further comprising a device having:
a sensor formed from a plurality of sensor elements embodied to enclose a whole circumference defined by the outer surface of the invasive instrument in a ring-shaped manner, wherein the sensor is embodied for reading the length-selective and rotation-selective pattern, wherein the sensor is embodied for temporary arrangement in a region of an opening of a body for insertion of the invasive instrument; and
a signal evaluator configured to simultaneously determine a penetration depth and a rotational orientation of the invasive instrument on the basis of the length-selective and rotation-selective pattern read by the sensor;
wherein the sensor is arranged in a ring-shaped housing; and
wherein the ring-shaped sensor has a plurality of optical waveguides, first ends of which are arranged in the ring-shaped housing in a ring-shaped manner and second ends of which are assigned to the plurality of sensor elements, which includes at least one of (i) CCD sensor elements, (ii) CMOS sensor elements, and (iii) reflection-light photoelectric sensor elements, and which are arranged in linear array-shaped manner.

18. The system of claim 17, wherein each arrangement of the regions of the length-selective and rotation-selective pattern also has a unique embodiment in the case of cyclical transposition of the regions.

19. The system of claim 17, wherein the signal evaluator is configured to simultaneously determine the penetration depth and the rotational orientation of the invasive instrument without first establishing a reference point for an orientation of the invasive instrument.

20. The system of claim 17, wherein the plurality of sensor elements of the sensor are configured in a uniformly distributed arrangement so as to enable a complete and uniform reading of the length-selective and rotation-selective pattern over the whole circumference defined of the outer surface of the invasive instrument.

21. A device for automatically evaluating penetration depth and rotational orientation of an invasive instrument during insertion of the invasive instrument into an opening of a body, the invasive instrument having an outer surface with a length-selective and rotation-selective pattern applied thereto, the device comprising:
a sensor formed from a plurality of sensor elements embodied to enclose a whole circumference of the outer surface of the invasive instrument in a ring-shaped manner, wherein the sensor is embodied for reading the length-selective and rotation-selective pattern, wherein the sensor is embodied for temporary arrangement in a region of the opening for the insertion of the invasive instrument; and
a signal processor configured to simultaneously determine a penetration depth and a rotational orientation of the invasive instrument on the basis of the length-selective and rotation-selective pattern read by the sensor;
wherein the sensor is arranged in a ring-shaped housing; and
wherein the ring-shaped sensor has a plurality of optical waveguides, first ends of which are arranged in the ring-shaped housing in a ring-shaped manner and second ends of which are assigned to the plurality of sensor elements, which includes at least one of (i) CCD sensor elements, (ii) CMOS sensor elements, and (iii) reflection-light photoelectric sensor elements, and which are arranged in linear array-shaped manner.

* * * * *